United States Patent
Ariga et al.

(10) Patent No.: US 9,207,156 B2
(45) Date of Patent: Dec. 8, 2015

(54) HARDNESS TESTER

(75) Inventors: Kozo Ariga, Tokyo (JP); Masaru Kawazoe, Yamato (JP)

(73) Assignee: MITUTOYO CORPORATION, Kanagawa (JP)

(*) Notice: Subject to any disclaimer, the term of this patent is extended or adjusted under 35 U.S.C. 154(b) by 13 days.

(21) Appl. No.: 13/453,197

(22) Filed: Apr. 23, 2012

(65) Prior Publication Data

US 2013/0047712 A1 Feb. 28, 2013

(30) Foreign Application Priority Data

Aug. 31, 2011 (JP) .................................. 2011-188472

(51) Int. Cl.
*G01N 3/42* (2006.01)

(52) U.S. Cl.
CPC .......... *G01N 3/42* (2013.01); *G01N 2203/0078* (2013.01)

(58) Field of Classification Search
CPC ............. G01N 3/40; G01N 3/42; G01N 3/48; G01N 2203/0078; G01N 2203/0076; G01N 2203/008; G01N 2203/0082
USPC ....................................................... 73/78, 81
See application file for complete search history.

(56) References Cited

U.S. PATENT DOCUMENTS

| | | | | |
|---|---|---|---|---|
| 4,613,573 A * | 9/1986 | Shibayama et al. | ....... | 435/286.3 |
| 4,667,509 A | 5/1987 | Tobolski et al. | | |
| 5,146,779 A * | 9/1992 | Sugimoto et al. | .................. | 73/81 |
| 5,479,252 A * | 12/1995 | Worster et al. | ............. | 356/237.5 |
| 5,682,489 A * | 10/1997 | Harrow et al. | ................. | 715/839 |
| 6,247,355 B1 * | 6/2001 | Suresh et al. | ...................... | 73/82 |
| 6,301,956 B1 * | 10/2001 | Fujita et al. | ....................... | 73/82 |
| 2004/0096093 A1 * | 5/2004 | Hauck et al. | .................. | 382/141 |
| 2004/0134263 A1 * | 7/2004 | Tsujii et al. | ....................... | 73/81 |
| 2007/0122143 A1 * | 5/2007 | Okamoto | ...................... | 396/432 |
| 2008/0198447 A1 * | 8/2008 | Swift et al. | .................... | 359/385 |
| 2009/0145196 A1 * | 6/2009 | Kawazoe et al. | ............. | 73/1.89 |

(Continued)

FOREIGN PATENT DOCUMENTS

| | | |
|---|---|---|
| CN | 1510410 | 7/2004 |
| CN | 101470061 | 7/2009 |

(Continued)

OTHER PUBLICATIONS

China Office Action, dated Apr. 23, 2014 along with an English translation thereof.

(Continued)

*Primary Examiner* — Hezron E Williams
*Assistant Examiner* — Marrit Eyassu
(74) *Attorney, Agent, or Firm* — Greenblum & Bernstein, P.L.C.

(57) ABSTRACT

A hardness tester that measures a size of an indent to determine the hardness of a sample. The hardness tester includes an imaging unit, a display unit, a pointing device and a position adjustment unit. The imaging unit takes an image of a surface of the sample. The display unit displays a surface image of the sample and a cursor. The pointing device receives a first instruction instructing a movement of the surface image of the sample appearing on the display unit through a movement of the cursor, and a second instruction instructing a change in a height of the sample stage through a movement of the cursor. The position adjustment unit moves the sample stage in a horizontal direction and in a vertical direction.

5 Claims, 8 Drawing Sheets

(56) References Cited

U.S. PATENT DOCUMENTS

| | | | |
|---|---|---|---|
| 2010/0166608 A1* | 7/2010 | Quan et al. | 422/68.1 |
| 2012/0085154 A1 | 4/2012 | Takemura et al. | |
| 2012/0087567 A1 | 4/2012 | Takemura et al. | |

FOREIGN PATENT DOCUMENTS

| | | |
|---|---|---|
| EP | 1632767 | 3/2006 |
| JP | 8-262327 | 10/1996 |
| JP | 2002-098897 | 4/2002 |
| JP | 2004-286542 | 10/2004 |
| JP | 2005-326169 | 11/2005 |
| JP | 2005-337974 | 12/2005 |
| JP | 2007-034050 | 2/2007 |
| JP | 2011-002247 | 1/2011 |

OTHER PUBLICATIONS

China Office action, dated Dec. 22, 2014 along with an English translation thereof.

Japan Office action, mail date is Mar. 24, 2015, together with an English-language translation.

Chinese Office Action, mailed Jun. 1, 2015 in Chinese Application No. 201210150255.7, along with an English translation thereof.

* cited by examiner

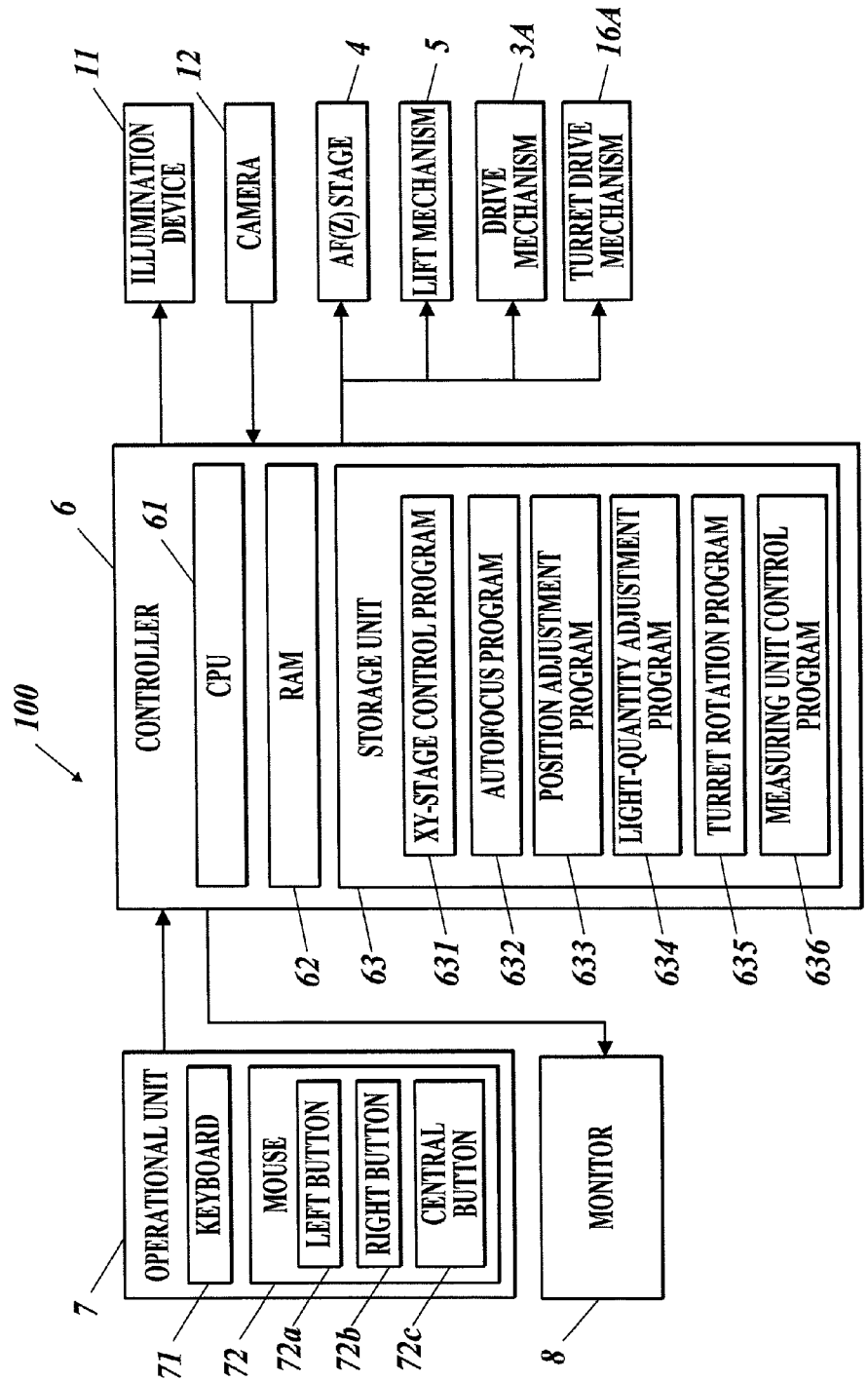

HARDNESS TESTER

BACKGROUND OF THE INVENTION

1. Field of the Invention

The present invention relates to a hardness tester.

2. Description of the Related Art

In a typical hardness tester, an indenter is urged to a surface of a sample to form an indent, and hardness of the sample is determined on the basis of the size of the indent.

For example, to determine hardness of a sample with a Vickers hardness tester, the sample is positioned in the horizontal direction such that a point to be indented on a surface of the sample lies directly below an indenter, while is positioned in the vertical direction (focusing) at the point. A turret is then rotated to allow the indenter to face the sample, and a predetermined testing force is applied to the sample surface through the indenter to form an indent. The diagonal length of the indent is then measured, and the hardness of the sample is calculated on the basis of the measured length of the diagonal of the indent.

For such positioning using the hardness tester, a monitor displays a surface image of a sample captured by a camera and appearing on a main screen and operational bars for adjusting horizontal and vertical positions of the surface image appearing on the main screen. A user adjusts the position of the sample through the operation of the operational bars with a keyboard or a mouse while viewing the surface image on the main screen.

Unfortunately, such a tester involves the operation of the operational bars provided separately from the main screen; hence, the user must turn its eyes from the main screen to the operational bars for every operation of the operational bars. This precludes operability of the tester.

To solve such a problem, for example, a technique (see Japanese Unexamined Patent Application Publication No. H8-262327) has been proposed to be used for a stage of a microscope or a machining table of a machine tool, in which starting and stopping points are set on a screen through mouse operation, the respective X-Y coordinates of the starting and stopping points are detected, the moving distances in X and Y directions of the X-Y table are set on the basis of the coordinate values, and consequently the X-Y table can be automatically moved to a target position.

According to the technique, the X-Y table can be simply and accurately moved to an appropriate position in any direction merely through setting of the starting and stopping points.

Unfortunately, since the technique described in Japanese Unexamined Patent Application Publication No. H8-262327 simply relates to setting of the starting and stopping points on a screen through a mouse operation, an image cannot be continuously moved on the screen, leading to a difficulty in fine position adjustment. As a result, the technique cannot be applied to a hardness tester that requires fine position adjustment for accurate measurement, resulting in low operability of the tester.

In addition, Japanese Unexamined Patent Application Publication No. H8-262327 has no description on vertical position adjustment; hence, the technique cannot solve the low operability in the adjustment of a vertical position.

SUMMARY OF THE INVENTION

The present invention has been made in consideration of the above situation, and one of the main objects of the present invention is to provide a hardness tester that is highly operable for adjustment of positions of a sample in both horizontal and vertical directions.

In order to achieve any one of the above advantages, according to an aspect of the present invention, there is provided a hardness tester that applies a predetermined testing force to a surface of a sample placed on a sample stage through an indenter to form an indent and measures the size of the indent to determine the hardness of the sample, the hardness tester including:

an imaging unit which takes an image of the surface of the sample through an objective lens;

a display unit which displays a surface image of the sample taken by the imaging unit and a cursor;

a pointing device which receives a first instruction instructing a movement of the surface image of the sample appearing on the display unit through a movement of the cursor, and a second instruction instructing a change in a height of the sample stage through a movement of the cursor; and a position adjustment unit which moves the sample stage in a horizontal direction in accordance with a movement of the cursor in response to the first instruction from a user, and moves the sample stage in a vertical direction in accordance with a movement of the cursor in response to the second instruction from the user.

BRIEF DESCRIPTION OF THE DRAWINGS

The present invention and the above-described objects, features and advantages thereof will become more fully understood from the following detailed description with the accompanying drawings and wherein;

FIG. 4 is a block diagram illustrating a control structure of the hardness tester shown in FIG. 1;

DETAILED DESCRIPTION OF THE PREFERRED EMBODIMENTS

A hardness tester according to an embodiment is now described in detail with reference to the accompanying drawings.

The configuration of a hardness tester 100 of the embodiment is described.

Figure 1:
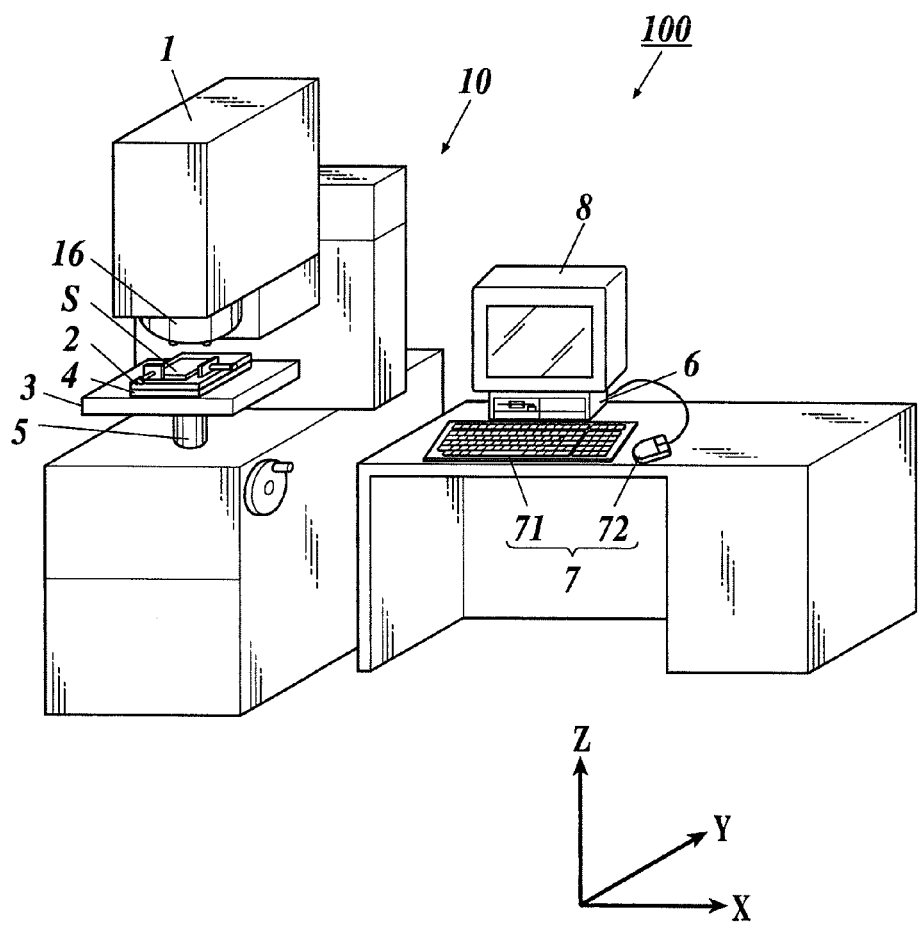
FIG. 1 is a schematic view illustrating an overall configuration of a hardness tester of the present invention.

As shown in FIG. 1, in the following description, the horizontal direction of the hardness tester 100 is defined as the X direction, the anteroposterior direction thereof as the Y direction, and the vertical direction as the Z direction.

The hardness tester 100 shown in FIG. 1 is, for example, a Vickers hardness tester, which includes a main unit 10, a controller 6, an operational unit 7, and a monitor 8.

Figure 2:
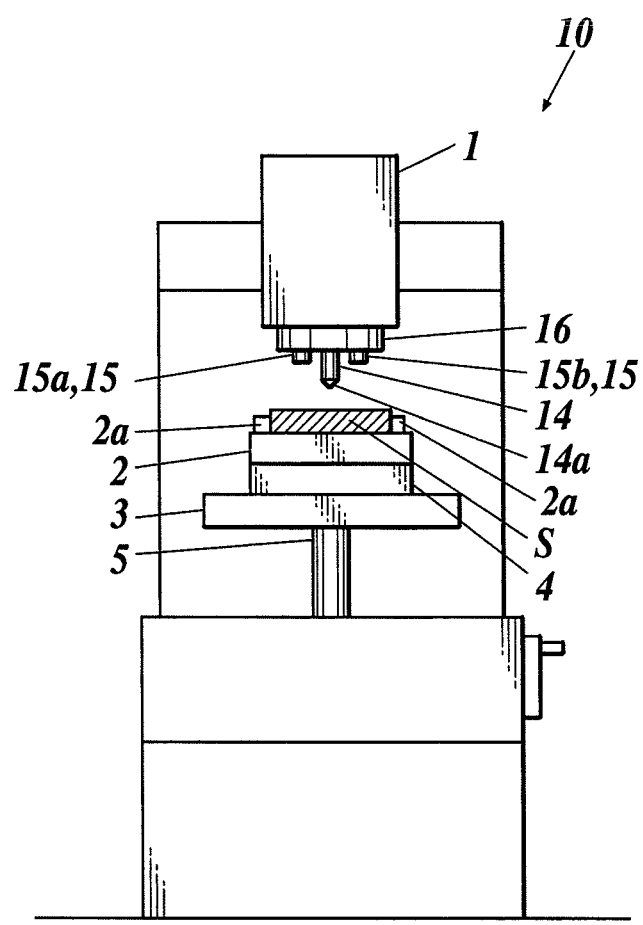
FIG. 2 is a schematic view illustrating a main unit of the hardness tester shown in FIG. 1.

With reference to FIG. 2, the main unit 10 includes, for example, a measuring unit 1 that measures the hardness of a sample S, a sample stage 2 on which the sample S is placed, an XY stage 3 that moves the sample stage 2 in the horizontal direction (XY direction), an autofocusing (AF) (Z) stage 4 that adjusts the focus to the surface of the sample S, and a lift mechanism 5 that vertically moves the sample stage 2 together with the XY stage 3 and the AF (Z) stage 4.

Figure 3:
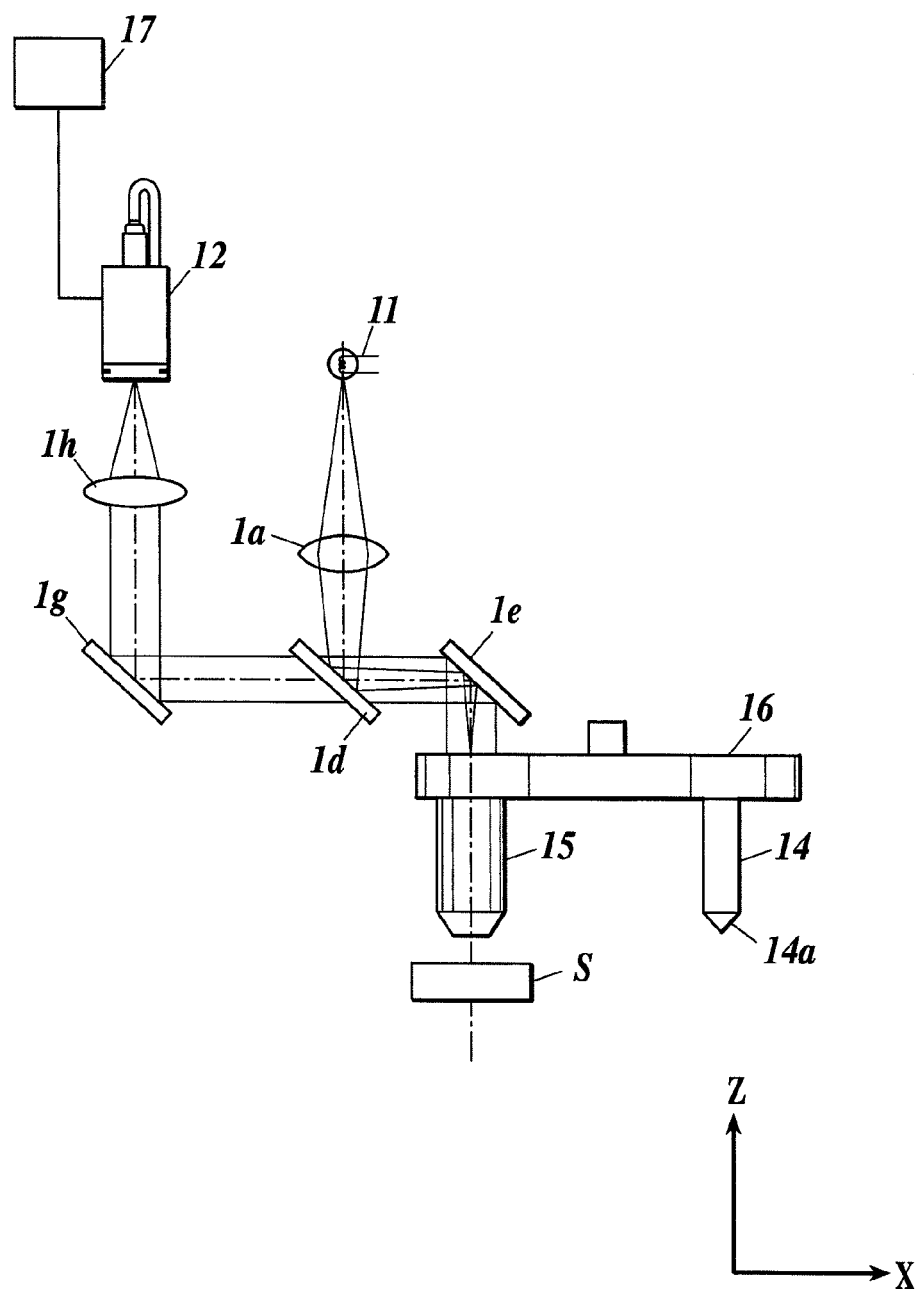
FIG. 3 is a schematic view illustrating a measuring unit of the hardness tester shown in FIG. 1.

With reference to FIG. 3, the measuring unit 1 includes, for example, an illumination device 11 that illuminates the surface of the sample S, a camera 12 that takes an image of the surface of the sample S, an indenter shaft 14 having an indenter 14a, objective lenses 15, and a turret 16 that is rotatable to allow switching of the indenter shaft 14 and either objective lens 15 from each other.

The illumination device 11 is an illuminating unit which illuminates the surface of the sample S with light. The light output from the illumination device 11 reaches the surface of the sample S through a lens 1a, a half mirror 1d, a mirror 1e, and an objective lens 15.

The camera 12 is an imaging unit. For example, as shown in FIG. 3, the camera 12 takes an image of the surface of the sample S and an image of an indent formed on the surface of the sample S by the indenter 14a on the basis of reflected light received by the camera from the surface of the sample S through the objective lens 15, the mirror 1e, the half mirror 1d, a mirror 1g, and a lens 1h, and thus acquires image data and outputs the image data to the controller 6.

The indenter shaft 14 is moved to the sample S placed on the sample stage 2 by a load mechanism (not shown) driven in response to control signals output from the controller 6, and urges the indenter 14a at the end of the indenter shaft 14 to the surface of the sample S at a predetermined force.

The objective lenses 15 include a plurality of condensing lenses having different magnifications, which are held on the bottom of the turret 16. Each condensing lens is positioned above the sample S through rotation of the turret 16 to uniformly apply the light from the illumination device 11 to the surface of the sample S.

In detail, the objective lenses 15 include a high-powered lens 15a and a low-powered lens 15b having a lower magnification than that of the high-powered lens 15a.

The high-powered lens 15a preferably has a magnification of 20 times or more, for example. The lens having such a magnification has a shallow focal depth that does not exceed the allowable height of the sample S for indentation, resulting in an improvement in vertical positioning accuracy of the sample S. In contrast, the low-powered lens 15b preferably has a magnification of 5 times or less, for example. The lens having such a magnification enables acquisition of a wide visual-field image, and thus a wide-area image can be readily acquired.

The turret 16 rotates about an axis in the Z axis direction by a turret drive mechanism 16A that operates in response to control signals output from the controller 6.

The turret 16 has a bottom having the indenter shaft 14 and the objective lenses 15 (the high-powered lens 15a and the low-powered lens 15b) thereon, and rotates about the axis in the Z axis direction to allow one of the indenter shaft 14 and the objective lenses 15 to be positioned above the sample S in a switchable manner. Specifically, the indenter shaft 14 is positioned above the sample S and then lowered to form an indent on the surface of the sample S, and either objective lens 15 is then positioned above the sample S in order to observe the formed indent.

The sample stage 2 has a sample fixer 2a to fix the sample S placed on the top of the sample stage 2.

The XY stage 3 is driven by the drive mechanism 3A that operates in response to control signals output from the controller 6, and moves the sample stage 2 in the X and Y directions perpendicular to the movement direction (Z direction) of the indenter 14a.

The AF stage 4 is driven in response to control signals output from the controller 6, and finely moves up and down the sample stage 2 on the basis of the image data taken by the camera 12 to adjust the focus to the surface of the sample S.

The lift mechanism 5 is driven in response to control signals output from the controller 6, and vertically moves the sample stage 2 together with the XY stage 3 and the AF (Z) stage 4 to vary the relative distance between the sample stage 2 and the objective lens 15.

The monitor 8 is a display unit, such as a liquid crystal display (LCD), which displays, for example, a surface image of the sample S and an image of the indent formed on the surface of the sample S taken by the camera 12.

The monitor 8 can also display a cursor K that moves on the monitor 8 through the operation of a mouse 72 (described below), in addition to the images.

The monitor 8 further displays set conditions of a hardness test sent from the operational unit 7, and results of the hardness test.

The operational unit 7 includes a keyboard 71 and a mouse 72.

Figure 5A:
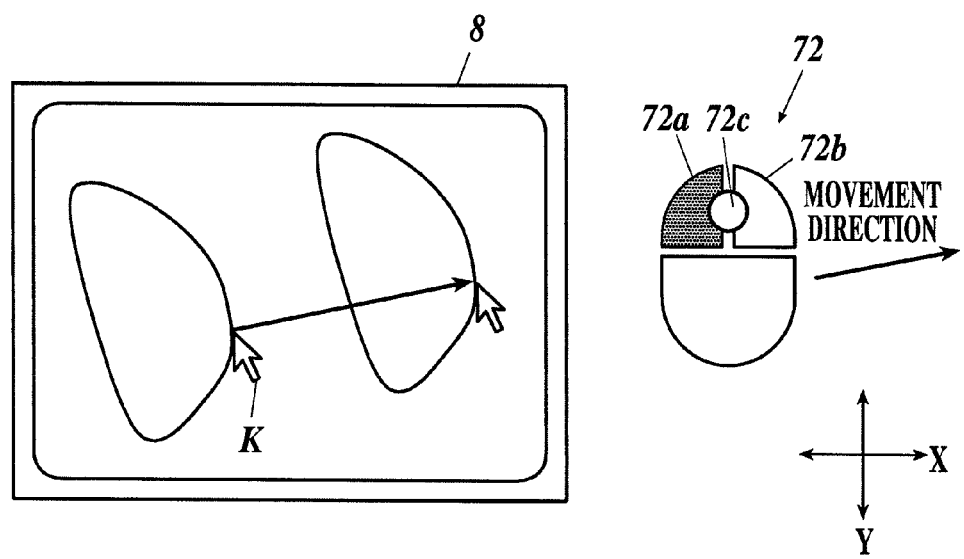
FIGS. 5A and 5B are schematic illustrations of an operation of the hardness tester of the present invention.

As shown in FIG. 5A, the mouse 72 includes a left button (first push button) 72a, a right button (second push button) 72b, and a central button (third push button) 72c, and is a pointing device that accepts a drag operation and other operations by a user.

In detail, the mouse 72 receives the following first to fourth instructions from a user, and outputs operational signals in response to the first to fourth instructions to the controller 6.

The first instruction is to move the displayed surface image of the sample S on the monitor 8 through the movement of the cursor K, and is executed by a drag operation with the mouse 72 in an appropriate direction while the left button 72a is depressed, for example, (see FIG. 5a).

Figure 6A:
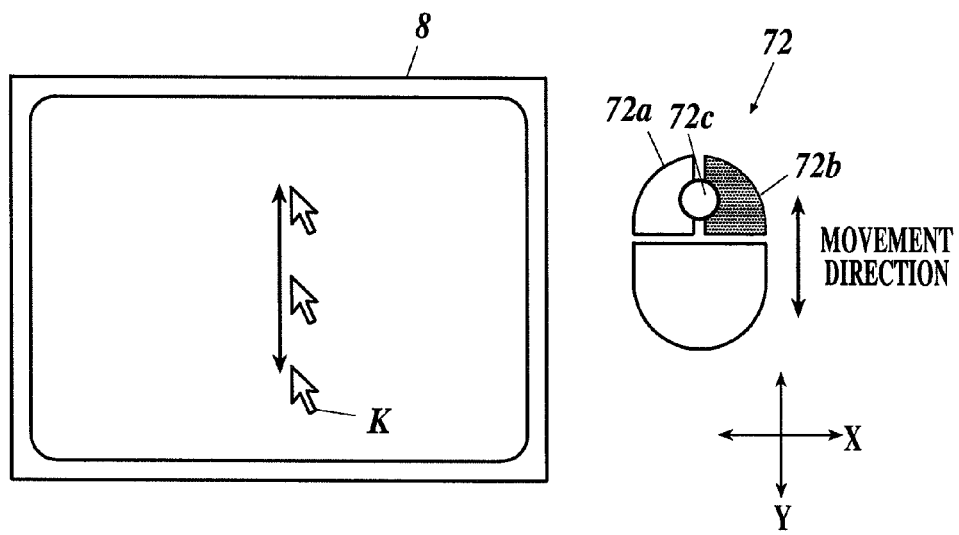
FIGS. 6A and 6B are schematic illustrations of another operation of the hardness tester of the present invention.

The second instruction is to change the height of the sample stage 2 through the movement of the cursor K, and is executed by a drag operation with the mouse 72 in a predetermined first direction (here, Y direction), which is beforehand set, while the right button 72b is depressed, for example, (see FIG. 6a).

Figure 7A:
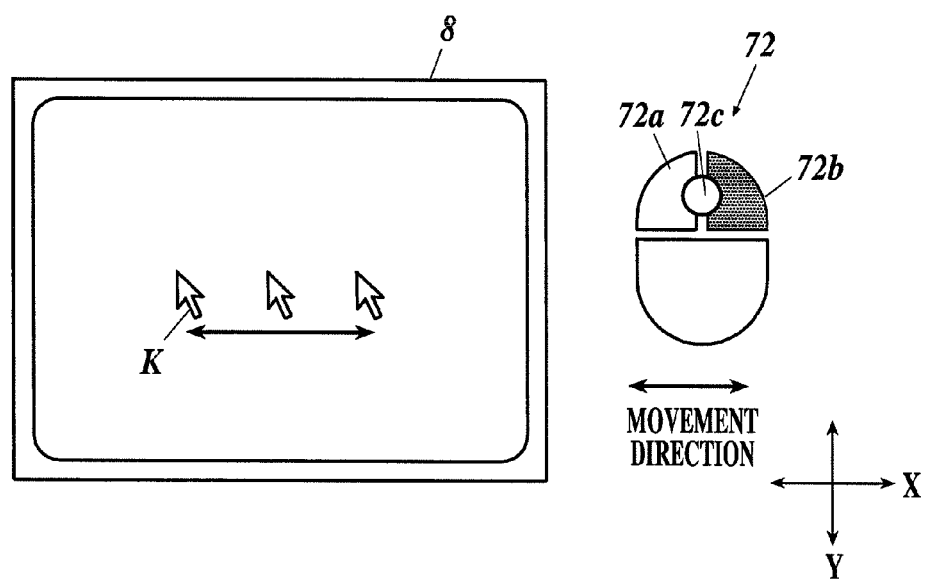
FIGS. 7A and 7B are schematic illustrations of another operation of the hardness tester of the present invention.

The third instruction is to change the brightness of a screen on the monitor 8 through the movement of the cursor K, and is executed by a drag operation with the mouse 72 in a predetermined second direction (here, X direction), which is beforehand set, while the right button 72b is depressed, for example, (see FIG. 7a).

Figure 8A:
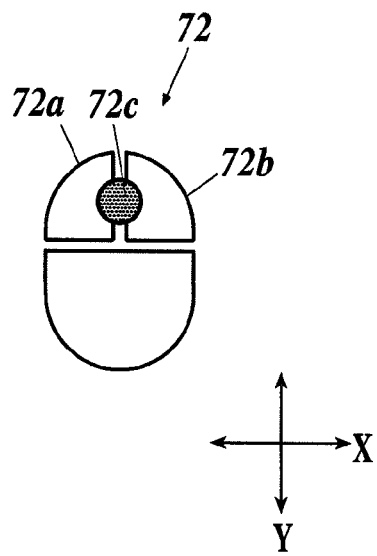
FIGS. 8A and 8B are schematic illustrations of another operation of the hardness tester of the present invention.

The fourth instruction is to change the magnification of the objective lens 15, and is executed by depressing the central button 72c, for example, (see FIG. 8a).

The specific operations of the mouse 72 for executing the first to fourth instructions can be appropriately set without limitation.

The arrows in FIGS. 5A, 6A, and 7A are virtual images for description of the drag operation, and do not appear on the actual monitor 8.

The operational unit 7 is used for other user operations such as setting of various conditions of a hardness test with the hardness tester 100. Specifically, upon receiving a predetermined operation by a user, the operational unit 7 sends predetermined signals corresponding to the operation to the controller 6.

The various conditions include, for example, test conditions such as the material of the sample S, the load (N) applied to the sample S from the indenter 14a, and the magnification of each objective lens 15; the test start point; the number of rows and columns; and the pitch.

As shown in FIG. 4, the controller 6 includes a central processing unit (CPU) 61, a random access memory (RAM) 62, and a storage unit 63, and controls the operations for a predetermined hardness test through execution of the predetermined programs stored in the storage unit 63.

The CPU 61 reads the programs including a processing program stored in the storage unit 63, expands the programs in the RAM 62, and executes the programs to control the overall hardness tester 100.

The RAM 62 expands the processing program and other programs executed by the CPU 61 in its program memory area, and stores input data and the processed results during execution of the processing program in its data memory area.

The storage unit 63 has, for example, a recording medium (not shown) including a semiconductor memory for storing the programs and data, and stores various types of data allowing the CPU 61 to control the overall hardness tester 100, various processing programs, and processed data during execution of the programs.

In detail, the storage unit 63 stores, for example, an XY-stage control program 631, an autofocus program 632, a position adjustment program 633, a light-quantity adjustment program 634, a turret rotation program 635, and a measuring-unit control program 636.

The CPU 61 executes the XY-stage control program 631 to control the position of the XY stage 3 such that the sample S faces the camera 12 after being placed on the sample stage 2, for example.

In detail, the CPU 61 executes the XY-stage control program 631 and activates the drive mechanism 3A to move the XY stage 3 such that the predetermined region of the surface of the sample S lies directly below the camera 12.

The CPU 61 executes the autofocus program 632 to automatically adjust the focus to the surface of the sample S, for example.

In detail, the CPU 61 executes the autofocus program 632 and vertically moves the AF (Z) stage 4 to automatically adjust the focus to the surface of the sample S on the basis of the image information from the camera 12 of the measuring unit 1.

For example, after execution of the XY-stage control program 631 and the autofocus program 632, if the mouse 72 receives the first instruction from a user, the CPU 61 executes the position adjustment program 633 to move the sample stage 2 in the horizontal direction (X and Y directions) in accordance with movement of the cursor K. If the mouse 72 receives the second instruction from a user, the CPU 61 executes the position adjustment program 633 to move the sample stage 2 in the vertical direction (Z direction) in accordance with movement of the cursor K.

In detail, if the mouse 72 receives the first or second instruction from the user, the mouse 72 sends operational signals including information on the movement direction and moving distance of the cursor K to the CPU 61.

If the mouse 72 receives the first instruction, the CPU 61 executes the position adjustment program 633 and activates the drive mechanism 3A to move the XY stage 3 in a direction corresponding to the movement direction of the cursor K by a distance corresponding to the moving distance of the cursor K so that the sample stage 2 is moved in the horizontal direction in accordance with the movement of the cursor K.

If the mouse 72 receives the second instruction, the CPU 61 executes the position adjustment program 633 and moves the AF (Z) stage 4 in a direction corresponding to the movement direction of the cursor K by a distance corresponding to the moving distance of the cursor K so that the sample stage 2 is moved in the vertical direction in accordance with the movement of the cursor K.

As a result, the image on the monitor 8 moves in accordance with the movement of the cursor K.

During this operation, the CPU 61 reads the magnification of the objective lens 15 facing the sample stage 2 and controls each component such that an increase in magnification of the objective lens 15 reduces the moving distance of the sample stage 2 corresponding to the moving distance of the cursor K in both the horizontal and vertical directions.

In detail, if a moving distance of the cursor K is about half the size of a screen, the moving distance of the sample stage 2 corresponding to the moving distance of the cursor K is 50 μm in both the horizontal and vertical directions for the high-powered lens 15a having a magnification of 50×, while it is 250 μm for the low-powered lens 15b having a magnification of 10×.

As a result, even if the range of an image varies after switching of the magnification of the objective lens 15, the sample stage 2 can be moved at a pitch suitable for the image.

Through execution of the position adjustment program 633, the CPU 61 functions as a position adjustment means together with the drive mechanism 3A and the AF (Z) stage 4.

For example, if the mouse 72 receives the third instruction from a user, the CPU 61 executes the light-quantity adjustment program 634 to vary the quantity of light from the illumination device 11 in accordance with the movement of the cursor K.

In detail, if the mouse 72 receives the third instruction from the user, the mouse 72 sends operational signals including information on the movement direction and the moving distance of the cursor K to the CPU 61.

The CPU 61 then executes the light-quantity adjustment program 634 to increase or decrease the quantity of light from the illumination device 11 by the quantity corresponding to the moving distance of the cursor K on the basis of the operational signals from the mouse 72.

Through execution of the light-quantity adjustment program 634, the CPU 61 functions as a light-quantity adjustment means.

For example, if the mouse 72 receives the fourth instruction from a user, the CPU 61 executes the turret rotation program 635 to rotate the turret 16.

In detail, if the mouse 72 receives the fourth instruction from the user, the mouse 72 sends operational signals including information on depression time of the central button 72c and other information to the CPU 61.

The CPU 61 then executes the turret rotation program 635, so that if the CPU 61 determines that the depression time exceeds a predetermined length, it controls the turret drive mechanism 16A to start rotation of the turret 16 and continue the rotation until the depression operation is stopped.

In a certain configuration, if the mouse 72 is dragged to the right while the central button 72c is depressed, the turret 16 is rotated clockwise, and if the mouse 72 is dragged to the left while the central button 72c is depressed, the turret 16 is rotated counterclockwise.

Through execution of the turret rotation program 635, the CPU 61 functions as a turret rotation means together with the turret drive mechanism 16A.

The CPU 61 executes the measuring-unit control program 636 so that the measuring unit 1 performs a predetermined operation, for example.

In detail, the CPU 61 executes the measuring-unit control program 636, and thus allows the indenter 14a to be urged to the surface of the sample S at a predetermined testing force in order to form an indent on the surface, measures the diagonal length of the indent on the basis of the image information of the surface of the sample S from the camera 12, and calculates the hardness of the sample S from the measured diagonal length of the indent.

The hardness tester 100 of the embodiment may not include the XY-stage control program 631 and the autofocus program 632.

The functions of the hardness tester 100 of the embodiment are now described.

In the hardness tester 100 having the above-described configuration, the XY stage 3, the AF (Z) stage 4, the illumination device 11, the turret 16 and others can be controlled through operation of the mouse 72.

Figure 5B:
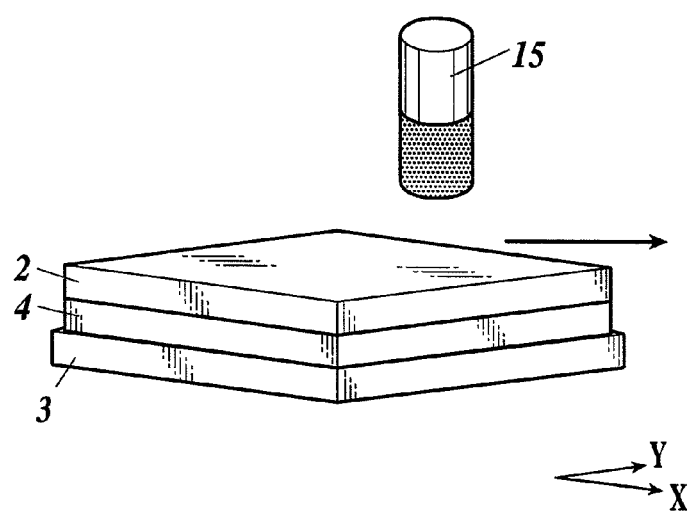

For example, as shown in FIGS. 5A and 5B, if the mouse 72 is dragged in an appropriate direction while the left button 72a is depressed in response to the first instruction, the XY stage 3 is moved in the horizontal direction so that an image on the monitor 8 moves in accordance with movement of the cursor K.

Figure 6B:
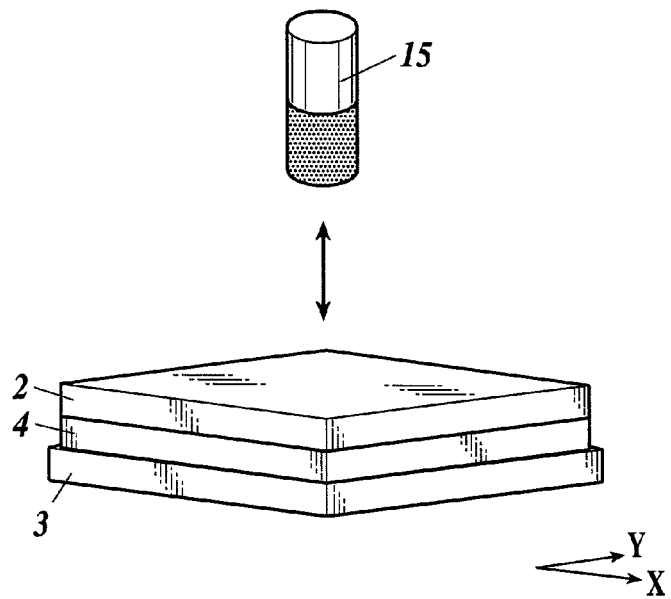

In addition, as shown in FIGS. 6A and 6B, if the mouse 72 is dragged in a predetermined first direction (here, Y direction) while the right button 72b is depressed in response to the second instruction, the AF(Z) stage 4 is moved in the vertical direction in accordance with movement of the cursor K on the monitor 8.

Figure 7B:
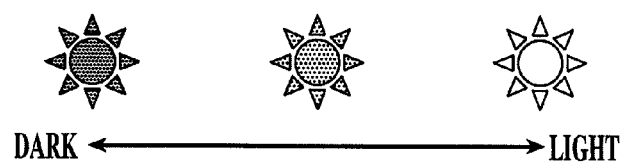

In addition, as shown in FIGS. 7A and 7B, if the mouse 72 is dragged in a predetermined second direction (here, X direction) while the right button 72b is depressed in response to the third instruction, the brightness of an image appearing on the monitor 8 is appropriately controlled in accordance with movement of the cursor K on the monitor 8.

Figure 8B:
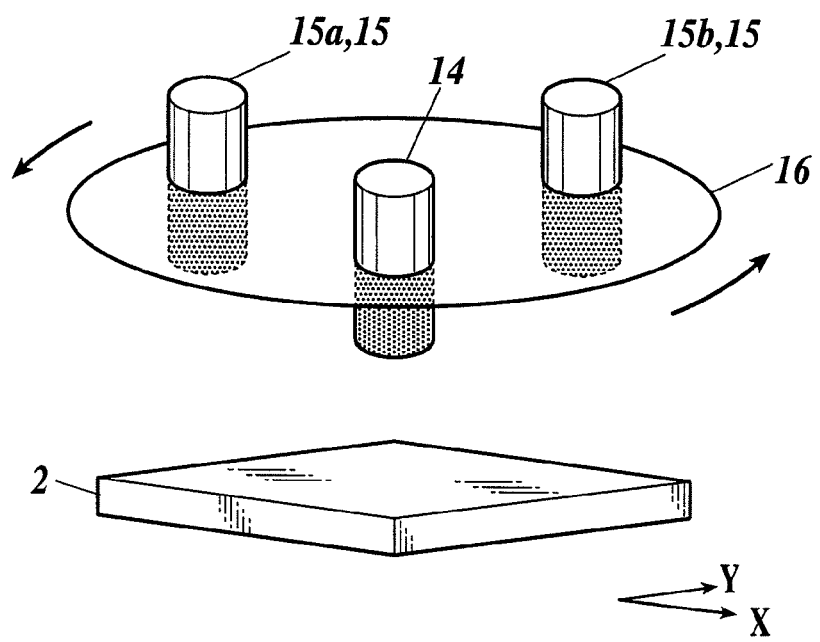

In addition, as shown in FIGS. 8A and 8B, if the central button 72c is depressed in response to the fourth instruction, the turret 16 is rotated for switching of the objective lens 15.

As described above, the hardness tester 100 of the embodiment includes the camera 12 that takes an image of the surface of the sample S through the objective lens 15; the monitor 8 that displays a surface image of the sample S taken by the camera 12 and the cursor K; the mouse 72 that receives the first instruction instructing horizontal movement of the surface image of the sample S appearing on the monitor 8 through movement of the cursor K and the second instruction instructing a change in the height of the sample stage 2 through movement of the cursor K; and the position adjustment means, including the CPU 61 and the position adjustment program 633, that moves the sample stage 2 in the horizontal direction in accordance with movement of the cursor K in response to the first instruction from a user, and moves the sample stage 2 in the vertical direction in accordance with movement of the cursor K in response to the second instruction from the user.

The mouse 72 has the left button 72a and the right button 72b, and accepts a drag operation by a user. The first instruction is executed through a drag operation of the mouse 72 while the left button 72a is depressed. The second instruction is executed through a drag operation of the mouse 72 in the predetermined first direction (Y direction) while the right button 72b is depressed.

As a result, the sample stage 2 is moved in both the horizontal and vertical directions only through an operation of the mouse 72.

In addition, the user can adjust the position of the sample S readily and finely in both the horizontal and vertical directions while watching the image appearing on the monitor 8.

In addition, operational bars for position adjustment and other operations need not be displayed on the monitor 8 in addition to a screen showing the surface image of the sample S, thus simplifying the screen configuration of the monitor 8.

As a result, the operability of the measurement can be improved.

In addition, the hardness tester 100 of the embodiment includes the mouse 72 that can accept the third instruction to vary the brightness of the screen appearing on the monitor 8 through movement of the cursor K; the illumination device 11 that illuminates the surface of the sample S with light; and the light-quantity adjustment means, including the CPU 61 and the light-quantity adjustment program 634, that varies the quantity of light from the illumination device 11 in accordance with movement of the cursor K in response to the third instruction from the user.

The third instruction is executed through a drag operation of the mouse 72 in the predetermined second direction (X direction) while the right button 72b is depressed by the user.

As a result, the quantity of light from the illumination device 11 to the surface of the sample S is varied only through an operation of the mouse 72, and consequently the user can adjust the brightness of the screen while watching an image appearing on the monitor 8.

As a result, the operability of the measurement can be further improved.

In addition, the hardness tester 100 of the embodiment includes the mouse 72 that accepts the fourth instruction to switch the magnification of the objective lens 15; the turret 16 having the indenter 14a and the plurality of objective lenses 15 thereon; and the turret rotation means, including the CPU 61 and the turret rotation program 635, that rotates the turret 16 in response to the fourth instruction from the user.

The mouse 72 has the central button 72c, and the fourth instruction is executed upon depression of the central button 72c by a user.

As a result, the objective lenses 15 can be switched from each other through an operation of the mouse 72, resulting in a further improvement in the operability of the measurement.

According to the hardness tester 100 of the embodiment, the position adjustment means controls each component such that an increase in the magnification of the objective lens 15 reduces the moving distance of the sample stage 2 corresponding to the moving distance of the cursor K in both the horizontal and vertical directions.

As a result, even if the hardness tester 100 has the plurality of objective lenses 15 having different magnifications and if the objective lenses 15 are switched from each other, the sample stage 2 is moved at a pitch corresponding to the relevant magnification, resulting in a further improvement in the operability of the measurement.

While the embodiment has been described with the exemplary configuration where the XY stage 3 or the AF (Z) stage 4 (sample stage 2) is moved in response to the first or second instruction through mouse operation, the camera 12 (the position of the objective lens 15) may be moved in both the horizontal and vertical directions instead.

In addition, directions may be displayed in the vicinity of the cursor K appearing on the monitor 8 to introduce the instruction operations of the mouse 72 and corresponding operations of the components of the hardness tester 100.

According to an aspect of the preferred embodiments of the present invention, there is provided a hardness tester that applies a predetermined testing force to a surface of a sample placed on a sample stage through an indenter to form an indent and measures the size of the indent to determine the hardness of the sample, the hardness tester including:

an imaging unit which takes an image of the surface of the sample through an objective lens;

a display unit which displays a surface image of the sample taken by the imaging unit and a cursor;

a pointing device which receives a first instruction instructing a movement of the surface image of the sample appearing on the display unit through a movement of the cursor, and a second instruction instructing a change in a height of the sample stage through a movement of the cursor; and a position adjustment unit which moves the sample stage in a horizontal direction in accordance with a movement of the cursor in response to the first instruction from a user, and moves the sample stage in a vertical direction in accordance with a movement of the cursor in response to the second instruction from the user.

According to the present invention, a display unit displays a surface image of a sample and a cursor, and a sample stage moves in a horizontal or vertical direction in conjunction with movement of the cursor on the display unit upon a predetermined instruction from a user with a pointing device.

Consequently, the sample stage can be moved in both horizontal and vertical directions only through the operation of the pointing device.

In addition, the user can adjust the position of the sample readily and finely in both the horizontal and vertical directions while watching the image appearing on the display unit.

In addition, operational bars for position adjustment and other operations need not be displayed on the display unit in addition to a screen displaying the surface image of the sample, simplifying the screen configuration of the display unit.

As a result, the operability of measurement can be improved.

Preferably, in the hardness tester, the pointing device has a first push button and a second push button, and accepts a drag operation by the user;

the first instruction is executed when the first push button is depressed while the pointing device is dragged by the user; and the second instruction is executed when the second push button is depressed while the pointing device is dragged in a predetermined first direction by the user.

Preferably, in the hardness tester, the pointing device accepts a third instruction for varying the brightness of a screen appearing on the display unit through movement of the cursor, and includes:

an illumination unit which applies light to the surface of the sample; and a light-quantity adjustment unit which varies the quantity of light from the illumination unit in accordance with movement of the cursor in response to the third instruction from the user.

Preferably, in the hardness tester, the third instruction is executed when the second push button is depressed while the pointing device is dragged in a predetermined second direction different from the first direction by the user.

Preferably, in the hardness tester, the pointing device accepts a fourth instruction for switching a magnification of the objective lens, and includes:

a turret having the indenter and the plurality of objective lenses thereon; and a turret rotation unit which rotates the turret in response to the fourth instruction from the user.

Preferably, in the hardness tester, the pointing device has a third push button; and the fourth instruction is executed upon depression of the third push button by the user.

Preferably, in the hardness tester, the position adjustment unit reduces a moving distance of the sample stage corresponding to a moving distance of the cursor in both horizontal and vertical directions with an increase in a magnification of the objective lens.

Although various exemplary embodiments have been shown and described, the invention is not limited to the embodiments shown. Therefore, the scope of the invention is intended to be limited solely by the scope of the claims that follow and not by the above explanation, and it is intended that the present invention covers modifications and variations that come within the scope of the appended claims and their equivalents.

The entire disclosure of Japanese Patent Application No. 2011-188472 filed on Aug. 31, 2011 including specification, claims, drawings and abstract are incorporated herein by reference in its entirety.

What is claimed is:

1. A hardness tester that applies a predetermined testing force to a surface of a sample placed on a sample stage through an indenter to form an indent and measures the size of the indent to determine the hardness of the sample, the hardness tester comprising:

an imager which takes an image of the surface of the sample through an objective lens;

a display which displays a surface image of the sample taken by the imager and a cursor;

a pointing device comprising a first push button which receives a first instruction instructing a movement of the surface image of the sample appearing on the display through a movement of the cursor, the pointing device further comprising a second push button which receives a second instruction instructing a change in a height of the sample stage through a movement of the cursor, wherein the pointing device is configured to accept a third instruction for varying the brightness of a screen appearing on the display through movement of the cursor;

an illuminator configured to apply light to the surface of the sample;

light-quantity adjuster which varies the quantity of light from the illuminator in accordance with movement of the cursor in response to the third instruction from the user, wherein the first instruction, the second instruction and the third instruction are received by the same pointing device; and a position adjuster, wherein:

in response to the first instruction from a user to move the cursor, first operational signals including movement direction and distance of the cursor are provided to a controller, wherein in accordance with the magnification of the objective lens and the movement of the cursor during a fine horizontal position adjustment procedure, the controller causes the position adjuster to move the sample stage in a horizontal direction by a first distance corresponding to the moving distance of the cursor, wherein the first instruction is executed when the first push button is depressed while the pointing device is dragged by the user, in response to the second instruction from the user to move the cursor, second operational signals including movement direction and distance of the cursor are provided to the controller, wherein in accordance with the magnification of the objective lens and the movement of the cursor during a fine vertical position adjustment procedure, the controller causes the position adjuster to move the sample stage in a vertical direction by a second distance corresponding to the moving distance of the cursor and automatically adjusts and maintains the focus of the imager to the surface of the sample, wherein the second instruction is executed when the second push button is depressed while the pointing device is dragged in a predetermined first direction by the user, and the third instruction is executed when the second push button is depressed while the pointing device is dragged in a predetermined second direction different from the first direction by the user.

2. The hardness tester according to claim 1, wherein the pointing device accepts a fourth instruction for switching a magnification of the objective lens, and includes:

a turret having the indenter and the plurality of objective lenses thereon; and a turret rotator which rotates the turret in response to the fourth instruction from the user.

3. The hardness tester according to claim 2, wherein the pointing device has a third push button; and the fourth instruction is executed upon depression of the third push button by the user.

4. The hardness tester according to claim 1, wherein the position adjuster reduces a moving distance of the sample stage corresponding to a moving distance of the cursor in both horizontal and vertical directions with an increase in a magnification of the objective lens.

5. The hardness tester according to claim 1, wherein:

the horizontal direction includes movement in a horizontal X-Y plane having an X movement component and a Y movement component; and the position adjuster is further configured to control the X and Y movement components of the horizontal direction at the same time.

* * * * *